United States Patent
Scalice et al.

(10) Patent No.: US 6,838,250 B2
(45) Date of Patent: Jan. 4, 2005

(54) IMMUNOASSAY FOR C-REACTIVE PROTEIN

(75) Inventors: Edward R. Scalice, Penfield, NY (US); John L. Daiss, Rochester, NY (US)

(73) Assignee: Ortho-Clinical Diagnostics, Inc., Rochester, NY (US)

(*) Notice: Subject to any disclaimer, the term of this patent is extended or adjusted under 35 U.S.C. 154(b) by 271 days.

(21) Appl. No.: 09/821,227

(22) Filed: Mar. 29, 2001

(65) Prior Publication Data

US 2002/0142356 A1 Oct. 3, 2002

Related U.S. Application Data (60) Provisional application No. 60/193,951, filed on Mar. 31, 2000.

(51) Int. Cl.[7] ............... C07K 16/18; C12N 5/20; G01N 33/543; G01N 33/577
(52) U.S. Cl. ............ 435/7.93; 435/7.1; 435/7.92; 435/70.21; 435/452; 435/327; 435/337; 435/965; 435/975; 436/518; 436/528; 436/548; 530/387.2; 530/388.25; 530/391.1
(58) Field of Search ................ 435/7.1, 7.92, 435/7.93, 70.21, 452, 327, 337, 965, 975; 436/518, 528, 548; 530/387.2, 388.25, 391.1

(56) References Cited

U.S. PATENT DOCUMENTS 4,699,880 A   10/1987   Goldstein
4,828,981 A   5/1989    Maggio
5,219,730 A   6/1993    Potocnjak et al.

FOREIGN PATENT DOCUMENTS

WO   WO 91/00872   1/1991

OTHER PUBLICATIONS

J. Michael Kilpatrick et al., "Demonstration of Calcium–Induced Conformational Change(s) In C–Reactive Protein By Using Monoclonal Antibodies", Molecular Immunology, 1982, pp. 1159–1165, vol. 19, No. 9, Pergamon Press Ltd., Great Britian.

Patrick Englebienne et al., "Water–Soluble Conductive Polymer Homogeneous Immunoassay (SOPHIA), A Novel Immunoassay Capable of Automation", Journal Immunological Methods, 1996, pp. 159–170, vol. 191, APE Associates, Ghislenghien, Belgium.

Search Report of European Application No. EP 01303068, the European application corresponding to the parent application of the present case.

*Primary Examiner*—Christopher L. Chin
*Assistant Examiner*—James L. Grun
(74) *Attorney, Agent, or Firm*—Stacey B. Antar (57) ABSTRACT

The present invention relates to new CRP immunoassay compositions. The compositions include a low affinity anti-human CRP monoclonal antibody, and an antiidiotypic antibody raised against it. The invention further provides a method for obtaining antiidiotypic monoclonal antibody populations directed to an antibody that is specific for a high concentration, high molecular weight target antigen.

10 Claims, 7 Drawing Sheets

Figure 1. Selection of low affinity antibody: Competitive Inhibition with Free CRP Assay Formats

ELISA Formats

Figure 4. DR in Thin Film using Spotted HRP Labels

Figure 5. DR Curves in thin film using Inkjet Applied Labels

Figure 6. Dr in Thin Film using Coated HRP Labels

ECi Formats

IMMUNOASSAY FOR C-REACTIVE PROTEIN

RELATED APPLICATIONS

This application claims priority to provisional application No. 60/193,951, filed Mar. 31, 2000.

FIELD OF THE INVENTION

The present invention relates an in vitro diagnostic immunoassay for detecting C-reactive protein (CRP).

BACKGROUND OF THE INVENTION

Most current immunoassays for high concentration, high molecular weight analytes are difficult to run on widely used clinical chemistry analyzers that use colorimetric or chemiluminescent detection systems.

Typically, immunoassays for high concentration, high molecular weight analytes in the marketplace are predicated on the multivalence of the analyte. Ultimately, the analyte is detected by some sort of cross-linking, either by agglutination (in turbidimetric or nephelometric assays), precipitation (radial immunodiffusion), or sandwich immunoassays. These types of immunoassays each have significant handicaps in translation into automated systems. Radial immunodiffusion assays are extremely slow (hours to days) and require substantial quantities of carefully selected antisera. Agglutination-based assays require both initial dilution and substantial quantities of immunomaterials. In addition, each of these methods requires specialized optical systems not ordinarily present on contemporary clinical analyzers. Sandwich or two-site immunoassays require either large initial dilutions or undesirably large concentrations of expensive immunomaterials.

The current capability of the formats directed to competitive immunoassays is best applied to high concentration, low molecular weight analytes like many therapeutic drugs or drugs of abuse. Traditionally, these competitive immunoassays are predicated on competition for a limited number of drug specific binding sites (immobilized antibody molecules) between free drug and an enzyme label prepared by chemical conjugation of a drug-derived hapten and horseradish peroxidase (HRP). Typically, selection criteria for the reagents for these diagnostic tests might include: first, the Kd (dissociation constant) of the drug:antibody complex must be similar to (within a factor of 10) the concentration of drug in the serum sample; and second, the Kd of the label:antibody complex must be substantially lower (one to several orders of magnitude depending on the absolute concentration of the analyte) than that of the drug:antibody complex under the same conditions. A problem encountered lies in the difficulty in making antibodies and labels with the necessary affinity requirements.

Satisfying the above conditions for high concentration, high molecular weight analytes is difficult. In particular the second condition (higher affinity for the labeled analyte), listed above is difficult to achieve. For small molecules, like drugs, the affinity of the antibody for the label can be enhanced by several effects including the "linker effect" (additional bonding energy due to interaction of the antibody with the linker), multisubstitution of the label with the hapten, and, possibly, favorable orientation of the drug on the label surface. Equivalent effects for macromolecular analytes are unlikely because the epitope for interaction with the analyte and the analyte:enzyme conjugate are identical and reside entirely on the analyte. Put another way, the analyte looks the same to the antibody whether it is free in solution or conjugated to an HRP molecule.

SUMMARY OF THE INVENTION

We have overcome the deficiencies of using the conventional approaches for detecting high concentration, low molecular weight analytes in a situation where the target analyte is high concentration, high molecular weight. Therefore, it is an object of the present invention to provide a method for obtaining antiidiotypic monoclonal antibody populations directed to an antibody that is specific for a high concentration, high molecular weight target antigen wherein said antiidiotypic antibody populations have a wide range of binding affinities for the selected antibody specific to said target antigen and wherein a subset of said antiidiotypic antibody populations can be selected having the required affinity for a particular application. In a preferred embodiment antiidiotypic antibody populations are selected which express an affinity for the antibody directed to the target antigen which is substantially greater than that of the target antigen for the antibody. Additionally, we describe a means for obtaining a low affinity antibody for the target antigen.

In another aspect, this invention relates to new CRP immunoassay compositions. Said compositions comprise the low affinity ($K_D \sim 10^{-7}$ M) anti-human CRP monoclonal antibody (CRP5-23), and an antiidiotypic antibody raised against CRP5-23. We found that CRP5-23 binding to CRP, advantageously, is insensitive to ionized calcium. The hybridoma for this antibody has been deposited on Feb. 16, 2000 with the ATCC with a designation of PTA-1354.

In yet another aspect, our invention relates generally to competitive immunoassay methods, dry-film and solution based elements and kits and specifically to an immunoassay for CRP.

Starting with an antibody having the appropriate affinity for the target analyte (antianalyte antibody) an antiidiotypic antibody can be prepared and selected having i) high affinity for the antianalyte antibody, and ii) which competes with target antigen in a mutually exclusive manner for binding to the antianalyte antibody.

We describe herein the development of a competitive enzyme immunoassay for human C-reactive protein based on the use of antiidiotypic antibodies which have a higher affinity than CRP for an anti-CRP antibody. The invention embodies two novel immunomaterials. The first is a relatively low affinity anti-human CRP monoclonal antibody, CRP5-23, which has the additional very useful property that its interaction with CRP is insensitive ($K_D$ differs by less than a factor of two when [$Ca^{++}$] is varied from 0 to 1 mM) to ionized calcium. The conformation of CRP is dependent upon calcium, and the fact that the binding of antibody and CRP is not so dependent is useful and in fact advantageous. As biological samples containing the antigen, CRP, may have varying calcium levels, the binding insensitivity is beneficial in an immunoassay for CRP.

The second immunomaterial is an antiidiotypic antibody raised against CRP5-23 and selected for its ability to compete with human CRP for binding to CRP5-23, such that binding of CRP and the antiidiotype antibody to CRP5-23 are mutually exclusive. A hybridoma capable of producing such an antiidiotypic antibody has been deposited with the ATCC on Feb. 16, 2000 and given the designation PTA-1353.

At least two previously issued U.S. Patents describe immunoassays that use antiidiotypic antibodies: U.S. Pat. No. 4,828,981, issued May 9, 1989, and U.S. Pat. No. 5,219,730, issued Jun. 15, 1993.

BRIEF DESCRIPTION OF THE DRAWINGS

FIGS. 3A and 3B: CRP dose response curves for each format in conventional microtiter plates. Both formats exhibit descending dose response curves with increasing CRP concentrations and the dose-response curve is positioned in the clinically relevant range for each assay. Format 1 is depicted in FIG. 3A; Format 2 in FIG. 3B. The absorbency at 414 nm reflects the amount of detectable HRP activity. In FIG. 3A, the closed diamonds define the dose-response curve obtained with the immobilized C23id2-6.3 and HRP-labeled CRP5-23; the closed squares define the response when CRP5-23 was substituted for the C23id2-6.3, as a control. In FIG. 3B, the closed squares define the dose-response curve obtained with immobilized CRP5-23 and HRP-labeled C23id2-6.3; the closed diamonds define the dose response curve when C23id2-6.3 was substituted for CRP5-23, as a control. Error bars indicate the average and standard deviation of duplicates.

FIG. 4: CRP dose-response curves of Formats 1 and 2 in thin film immunoassays using spotted labels. In each format the immobilized antibody was incorporated into a thin dry film by coating methods well known in the art. The HRP-labeled reagent was mixed with the CRP-containing sample and the mixture spotted onto the center of the thin film. After a five minute incubation, the thin film was washed by the controlled addition of wash fluid to drive the unbound elements to the margins of the incubation zone. The bound fraction (HRP activity) was measured by the simultaneous addition of peroxide which initiated color development from a dye previously incorporated into the thin film. Maximum rate of color development ($V_{max}$) is plotted as a function of [CRP]. Format 1 is presented in closed squares; Format 2 in closed circles.

FIG. 6: CRP dose-response curves in thin-film immunoassays using labels incorporated by gravure printing. HRP-conjugates were incorporated by gravure printing onto immuno-rate thin-film coatings containing the immobilized complementary antibody. Serum samples containing CRP at various concentrations were spotted onto coatings prepared in each format. After a five minute incubation, the thin film was washed by the controlled addition of wash fluid to drive the unbound elements to the margins of the incubation zone. The bound fraction (HRP activity) was measured by the simultaneous addition of peroxide which initiated color development from a dye previously incorporated into the thin film. Maximum rate of color development ($V_{max}$) is plotted as a function of [CRP]. Format 1 is presented in closed circles; Format 2 in closed squares.

DETAILED DESCRIPTION

Antiidiotypic antibody as used herein, is, by definition, an antibody which binds to the $V_H$ and/or $V_L$ domain of the cognate antibody, in this case CRP5-23. In this instance, the antiidiotypic has the additional property that its binding to its cognate antibody is mutually exclusive with the binding of the analyte CRP.

A "sample" as used herein, refers to any substance which may contain the analyte of interest. A sample can be biological fluid, such as whole blood or whole blood components including red blood cells, white blood cells, platelets, serum and plasma, ascites, urine, cerebrospinal fluid, and other constituents of the body which may contain the analyte of interest. optionally, samples may be obtained from water, soil, and vegetation.

A competitive immunoassay refers to an immunoassay that is designed so that the analyte to be measured and a labeled detector molecule compete for a limited number of mutually exclusive binding sites. In these types of immunoassays the abundance of the analyte is inversely related to the binding of the detector molecule.

The assay can be carried out using any enzyme label that can be attached to the detector molecule to form a labeled detector molecule. Enzymes such as oxidases, e.g., glucose oxidase, peroxidases, e.g., horseradish peroxidase (HRP), alkaline phosphatase and galactosidases are preferred labels.

It is within the skill of the ordinary artisan, for example a worker in clinical chemistry to determine a suitable substrate for a given label. The substrate can be a material which is directly acted upon by the enzyme label or a material that is involved in a series of reactions which involve enzymatic reaction of the label.

Other labels that can be effectively used in the invention are: fluorescent labels, e.g., fluorescein, dansyl; chemiluminescent labels and radioactive labels including, e.g., $^{125}I$ or $^{14}C$.

The effectiveness and advantages of the invention are further illustrated by the following examples. The examples are meant to illustrate, but not to limit, the scope and spirit of the invention.

EXAMPLE 1

Preparation of a low affinity antiCRP monoclonal antibody.

Figure 1:
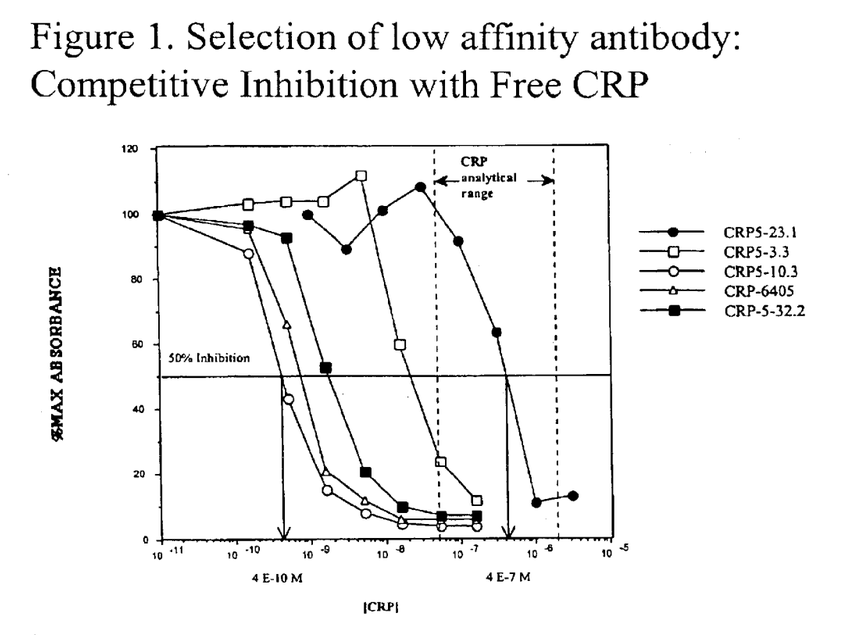
FIG. 1: shows a graph depicting the estimation of affinity constants from competition profiles of antiCRP antibodies and soluble CRP in ELISA. Competition profiles from five antibodies to CRP are shown which exhibit a range of affinities as determined by the concentration of CRP that yields a 50% reduction of the maximal absorbence. The normal range for CRP in human sera is indicated by vertical lines. The nominal affinities values for CRP5-10 (0.4 nM) and CRP5-23 (0.4 μM) are indicated by arrows projected onto the x-axis.

The concentration range of C-reactive protein found in human serum runs from a normal value of less than 5 mg/L (40 nM) to greater than 300 mg/L (2.6 μM). To devise a suitable competitive immunoassay for CRP required a monoclonal antibody having a Kd for CRP within the same concentration range, that is, between 40 nM and 2.6 μM. Monoclonal antibodies to CRP were generated following immunization of CAF1 mice with CRP-Limulus Hemocyanin conjugates and screened for binding to CRP by ELISA. Resulting CRP reactive cultures were cloned and their secreted antibodies measured for affinity to CRP using a competitive ELISA technique. The antibody cultures were initially titered on a CRP ELISA plate to determine the concentration at which the maximal absorbence value reaches a plateau. The minimal concentration at which the plateau maximal absorbence occurs was used in a competitive ELISA to assure that the antibody concentration is limiting. Soluble CRP at various concentrations was mixed with sample antibody then applied to the ELISA plate to generate an inhibition profile. The concentration that yielded 50% reduction of the maximal absorbence value approximates the Kd of the antibody:CRP interaction. FIG. 1 illustrates the affinity measurements of several antibodies derived from their inhibition profiles. Antibody CRP5-23 (IgG1,k) exhibited a Kd of 0.4 μM which met the first essential criterion (relatively low affinity for the analyte) for devising a competitive immunoassay for CRP.

EXAMPLE 2

Preparation of an antiidiotypic antibody to CRP5-23.

CAF1 mice were immunized with CRP5-23 antibody conjugated to Limulus hemocyanin. The mice were sacrificed and splenocytes obtained from the immunized mice were fused with SP2/0-Ag14 myeloma cells. The resulting hybridomas were initially screened by conventional ELISA for the secretion of antibody that bound to immobilized Fab fragments prepared from CRP5-23. This screen defined a population of antibodies with nominal reactivity for the CRP5-23 Fab fragment.

Further selection was performed to identify those antibodies with properties essential for competitive immunoassay. The criteria used for selecting a suitable antiidiotypic antibody were:

1. it should bind to CRP5-23 with relatively high affinity (Kd<$10^{-8}$ M), and
2. its binding to CRP5-23 should be mutually exclusive with binding of the analyte, CRP.

Positive clones were rescreened using surface plasmon resonance using a Biacore instrument to measure the affinity of the antiidiotypic antibody for CRP5-23 (as reflected in its off-rate) and the mutual exclusivity of binding. Rabbit anti-mouse IgG(Fc) was immobilized onto the biosensor surface and used to capture antiidiotypic antibodies from hybridoma culture supernates. CRP5-23 Fab fragments at 0.2 nM alone and in the presence of 0.9 nM CRP were injected over the surface of the immobilized antiidiotypic antibody and the relative mass accumulation compared. One antiidiotype antibody, C23id2-6.3 (IgG1,κ), met our criteria for an antiidiotypic antibody. It bound the Fab fragment of CRP5-23 with seemingly high affinity as indicated by its very slow off rate from the biosensor surface and its binding was inhibited by about ~33% in the presence of the relatively low concentration of CRP used as competitor.

EXAMPLE 3

Preparation of a competitive immunoassay using antiidiotypic antibodies in conventional ELISA.

Figure 2A:
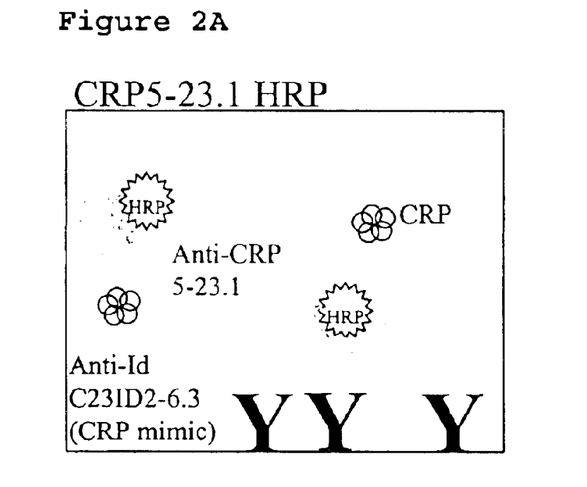
FIGS. 2A and 2B: depicts the two formats in which competitive immunoassays can be configured using a low affinity antiCRP antibody and its corresponding antiidiotypic antibody. In Format 1 (FIG. 2A), the antiidiotypic antibody C23id2-6.3, which serves as a CRP surrogate, is immobilized on the surface of a plastic microtiter plate. HRP-conjugated antiCRP monoclonal antibody CRP5-23 is added to the well along with sample containing CRP. The amount of CRP is ultimately reflected in the amount of HRP-CRP5-23 that binds to the immobilized antiidiotypic antibody. In Format 2 (FIG.2B), the CRP5-23 monoclonal antibody is immobilized and the HRP-conjugated antiidiotypic antibody competes with CRP in the sample for the CRP5-23 binding sites.
Figure 2B:
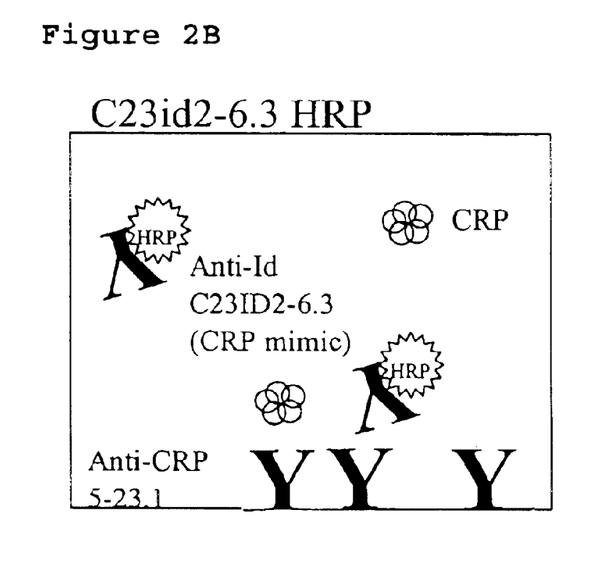
Figure 3A:
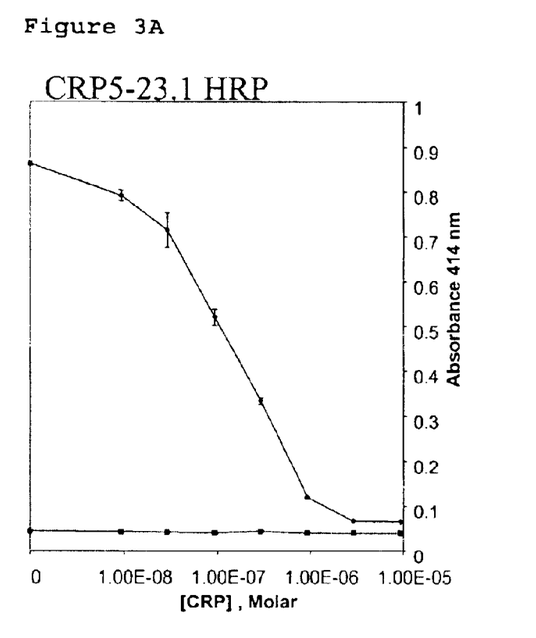
Figure 3B:
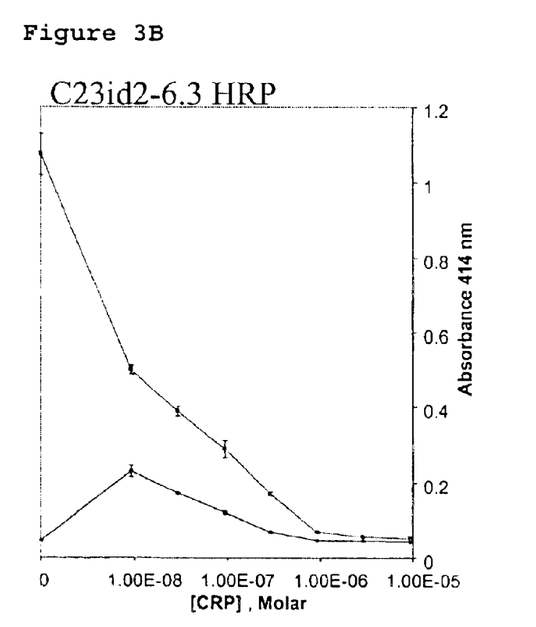

Two versions of ELISA format based competitive immunoassays were developed using the anti-CRP antibody CRP5-23 and its antiidiotype C23id2-6.3 along with their HRP conjugated partners. The two ELISA formats are illustrated in FIGS. 2A and 2B and the corresponding dose-response curves for CRP are presented in FIGS. 3A and 3B. As depicted in FIG. 2A, format 1 consists of the antiidiotypic antibody immobilized onto the plate surface and the HRP-labeled anti-CRP antibody competes with soluble CRP for sites on the immobilized antiidiotypic antibody. Format 2 in FIG. 2B uses the opposite orientation of reagents wherein the anti-CRP antibody is immobilized while the HRP-labeled antiidiotypic antibody and CRP in solution compete for antiCRP sites on the plate. Standard ELISA procedures were followed to immobilize antibody, block non-specific sites, titer labels, and for signal generation and detection. Decreasing dose-response curves with increasing CRP concentrations were observed using both formats, as illustrated.

EXAMPLE 4

Generation of dose-response curves for CRP using antiidiotypic antibodies in dry-film formats with soluble labels.

Figure 4:
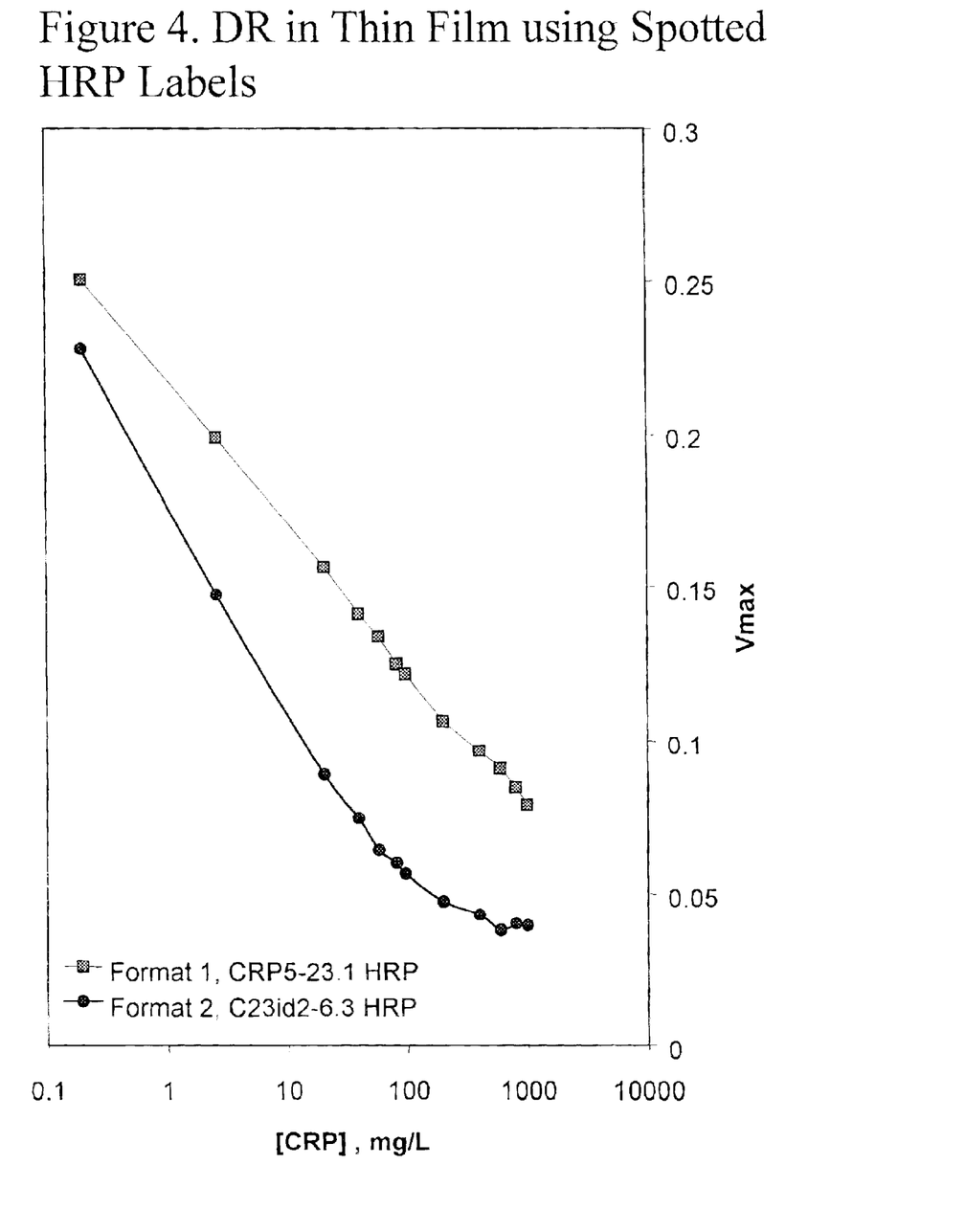

Having demonstrated that these immunomaterials work well AL in ELISA formats, we examined their utility in dry-film format. immuno-rate coatings were made for each format. Format 1 coatings consisted of antiidiotypic antibody C23id2-6.3 immobilized onto beads and coated in either the receptor or spreading layers. Coatings were then evaluated by adding soluble HRP-labeled anti-CRP antibody CRP5-23 to serum samples and run on VITROS® 250 analyzer using standard immuno-rate procedures. Format 2 coatings were manufactured and evaluated similarly except that they consisted of anti-CRP antibody CRP5-23 immobilized onto beads and HRP labeled antiidiotypic antibody was added to each sample. FIG. 4 illustrates one example for each format of a dose-response curve for CRP. Both formats exhibit descending dose-response curves with increasing CRP concentrations and the curves decline throughout the clinically relevant range for CRP.

EXAMPLE 5

Generation of a dose-response curve for CRP using antiidiotypic antibodies in dry-film formats using coated labels.

Figure 5:
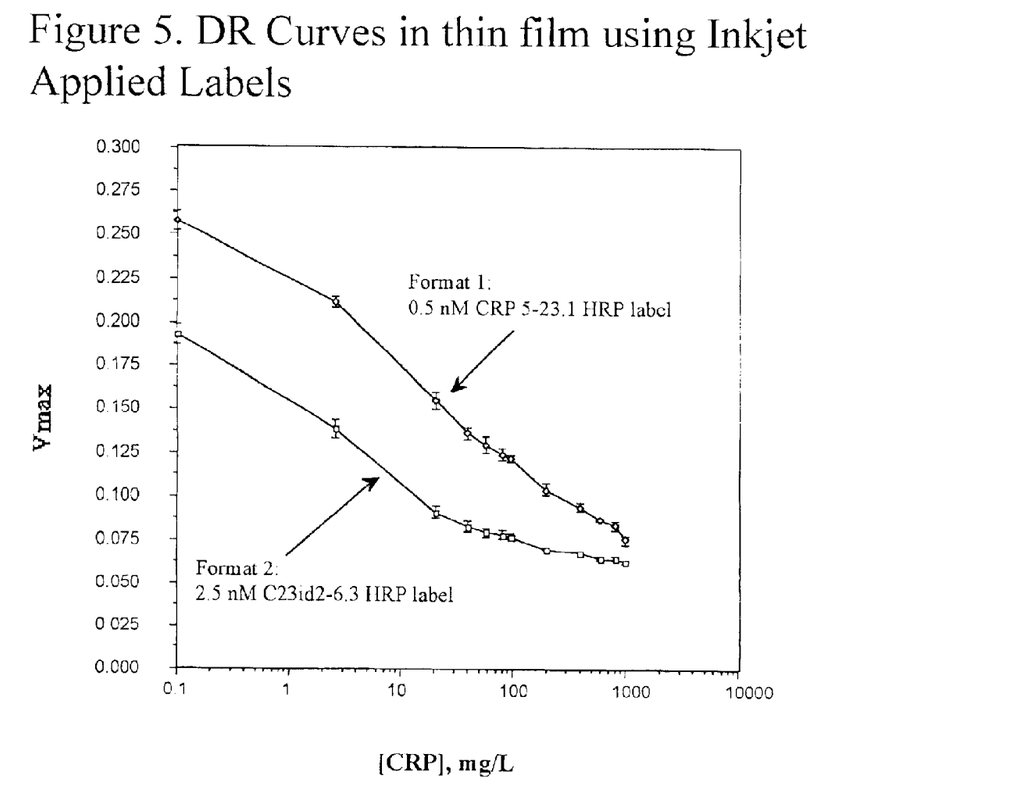
FIG. 5: CRP dose-response curves in thin film immunoassays using labels incorporated by inkjet printing. Format 1 is shown in closed squares; Format 2 in closed diamonds.

To demonstrate utility of these immunomaterials in dry-film, the HRP labels were incorporated into both format coatings using an inkjet printing process. For Format 1 HRP-conjugated CRP5-23 was applied onto a dry film coating containing immobilized C23id2-6.3. Its nominal concentration after rewetting by 10 μL of a serum sample was 2.5 nM IgG. Similarly, HRP-conjugated C23id2-6.3 was applied onto dry-film coating containing immobilized CRP5-23 to approximate a final concentration upon rewetting with 10 μL of a serum sample of 0.5 nM IgG. The inkjet-printed coatings were allowed to dry, then serum samples at various CRP concentrations were evaluated as immuno-rate assays on the VITROS®-250 analyzer. Both formats yielded descending dose-response curves with increasing CRP concentrations as shown in FIG. 5.

EXAMPLE 6

Generation of a dose-response curve for CRP in fully manufactured immuno-rate dry slide film format.

Figure 6:
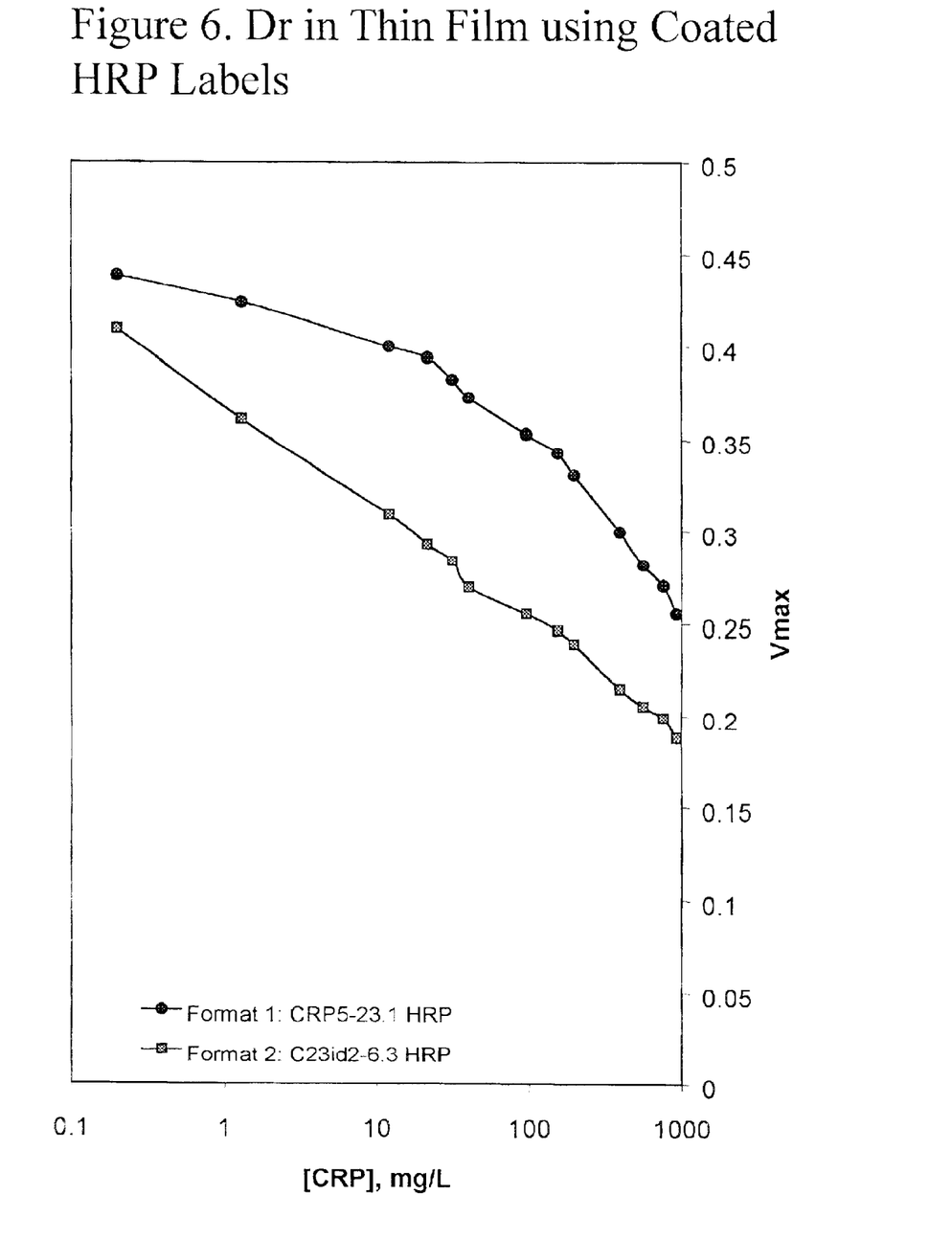

A process for manufacturing of this dry film is described. A complete immuno-rate coating was prepared as described for Format 1 previously. The anti-CRP HRP label was then incorporated into the dry film using the immuno-rate gravure cylinder printing process. The complete machine manufactured coating was slit, mounted and tested on an VITROS® 250 analyzer with serum based samples of varying CRP concentrations. The resulting descending dose response curve with increasing CRP concentration can be used to measure CRP values of unknown samples within the analyte range for CRP without dilution or pretreatment (see FIG. 6).

EXAMPLE 7

Generation of dose-response curves for CRP using anti-idiotypic antibodies on the VITROS® ECi automated immunoassay analyzer.

Figure 7A:
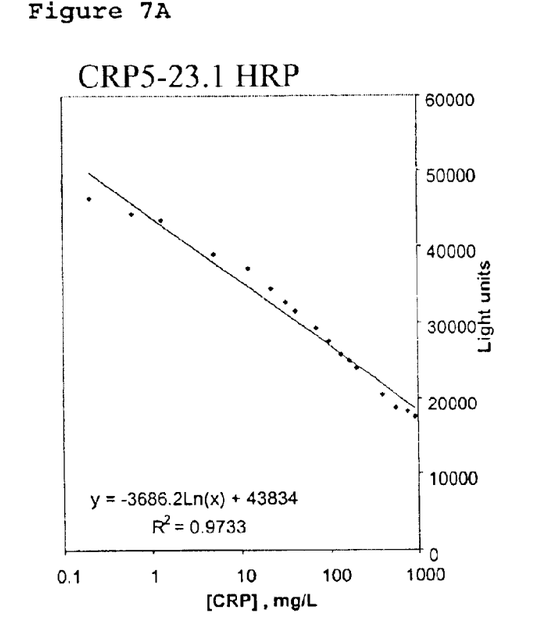
FIGS. 7A and 7B: CRP dose-response curve from immunoassays configured for the VITROS® ECi automated immunoassay analyzer system. In these variations the immobilized component is conjugated with biotin and present initially as a soluble component. 50 μL of the biotinylated reagent was added to streptavidin-coated well after the addition of 40 μL of CRP-containing sample and before the addition of 50 μL of the HRP-conjugated reagent. After an incubation of 8 minutes, the well was exhaustively washed and the well-associated HRP activity was detected by means of a chemiluminescent substrate. Format 1 is depicted in FIG. 7A; Format 2 in FIG. 7B.
Figure 7B:
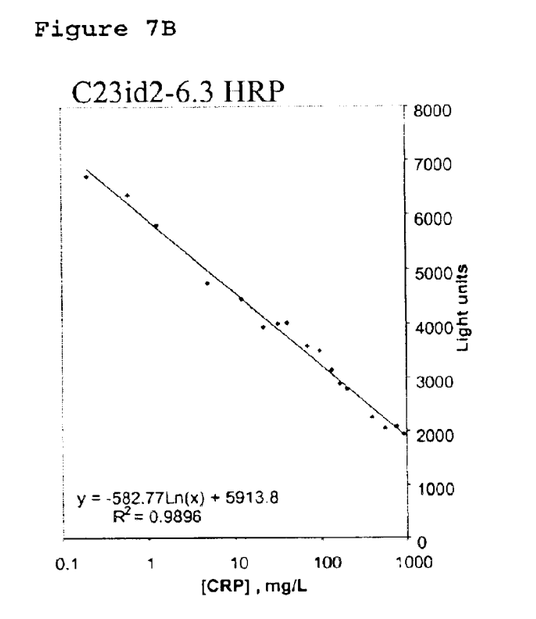

For Format 1, CRP5-23.1 was conjugated with HRP and C23id2-6.3 was conjugated with biotin by conventional methods. Depicted in FIG. 7A, a dose-response curve was generated using samples with CRP concentrations varying from 0.1 to 1000 mg/L. Similar data for Format 2 is presented in FIG. 7B.

Some advantages that were seen in immunoassays constructed with immunomaterials of the present invention are:

1. competitive immunoassays readily adapted to a variety of formats;
2. Analytic range: the analytic range is about two orders of magnitude wide, and is within the known useful range of CRP concentrations in human sera. The analytic range can be subtly repositioned by the concentrations of the primary components and the selection of which component is immobilized and which is mobile;
3. Versatility: These assays can be configured in more than one way. Two examples of configurations contemplated in the present invention are:
   i. with CRP5-23 immobilized and the HRP conjugate of the antiidiotypic antibody mobile, and
   ii. the antiidiotypic antibody immobilized and the HRP conjugate of CRP5-23 mobile;
4. Dilution: No dilution is required; however, should dilution be desirable for other reasons similar immunomaterials can be selected to accommodate the reduction in concentration of analyte;
5. Small materials requirements: where certain of the alternative methods require substantial dilution or undesirably large quantities of immunomaterials, these formats require only 1–10 nM of each (on the order of micrograms per assay); and
6. Reduction of susceptibility to heterophile activity in patient samples: antiCRP and antiidiotypic antibodies can be selected or modified so that they are of different heavy chain subclasses.

It is to be understood that numerous changes and modifications may be made therein without departing from the scope and intent of the invention.

We claim:

1. A method for performing a competitive immunoassay for detecting C-reactive protein in a sample containing an amount of C-reactive protein comprising:
   contacting the sample with an immobilized, a low affinity anti-human C-reactive protein antibody and a labeled antiidiotypic antibody, wherein the labeled antiidiotypic antibody binds to the anti-human C-reactive protein antibody and inhibits binding to the C-reactive protein.
   ii. detecting the label, and
   iii. correlating the detection of the label with the amount of C-reactive protein in the sample.

2. A method for performing a competitive immunoassay for detecting C-reactive protein in a sample containing an amount of C-reactive protein comprising:
   i. contacting the sample with an immobilized antiidiotypic antibody and a labeled low affinity anti-human C-reactive protein antibody, wherein the antiidiotypic antibody binds to the labeled anti-human C-reactive protein antibody and inhibits binding to the C-reactive protein,
   ii. detecting the label, and
   iii. correlating the detection of the label with the amount of C-reactive protein in the sample.

3. The method of claim 1 wherein the low affinity anti-human C-reactive protein antibody is CRP5-23 monoclonal antibody produced by a hybridoma deposited as PTA-1354.

4. The method of claim 2 wherein the antiidiotypic antibody binds CRP5-23 monoclonal antibody produced by a hybridoma deposited as PTA-1354.

5. A kit for a competitive immunoassay comprising: a first antibody wherein said first antibody is a low affinity anti-human C-reactive protein antibody and a second antibody wherein said second antibody is an antiidiotypic antibody which binds to said first antibody and inhibits binding of C-reactive protein to said first antibody.

6. A hybridoma cell line, identified as CRP5-23 and deposited as PTA-1354, capable of producing a low affinity anti-human C-reactive protein monoclonal antibody.

7. An antibody produced by the hybridoma of claim 6.

8. The antibody of claim 7 wherein said antibody is insensitive to ionized calcium.

9. A purified, isolated antiidiotypic antibody raised against a low affinity anti-human C-reactive protein antibody, which is capable of binding to CRP5-23 with relatively high affinity (Kd <$10^{-8}$M), and its binding to CRP5-23 is mutually exclusive with binding of C-reactive protein.

10. A hybridoma cell line, identified as C23id2-6.3 and deposited as PTA-1353, capable of producing an antiidiotypic monoclonal antibody.

* * * * *